United States Patent [19]

Kuchar et al.

[11] Patent Number: 5,386,071
[45] Date of Patent: Jan. 31, 1995

[54] PROCESS FOR PRODUCING AROMATICS FROM A $C_5/C_6$ FEEDSTREAM

[75] Inventors: Paul J. Kuchar, Hinsdale; Christopher D. Gosling, Roselle, both of Ill.

[73] Assignee: UOP, Des Plaines, Ill.

[21] Appl. No.: 154,893

[22] Filed: Nov. 19, 1993

[51] Int. Cl.[6] .......................... C07C 1/00; C07C 15/00
[52] U.S. Cl. .................... 585/313; 585/322; 585/413; 585/417; 502/20
[58] Field of Search ............... 585/313, 322, 413, 417; 502/20

[56] References Cited

U.S. PATENT DOCUMENTS 4,806,700  2/1989  Montindale ..................... 585/322
5,258,563  11/1993  Gosling et al. .................. 585/322

*Primary Examiner*—Helen M. S. Sneed
*Assistant Examiner*—Nhat D. Phan
*Attorney, Agent, or Firm*—Thomas K. McBride; Eugene I. Snyder; Frank S. Molinaro

[57] ABSTRACT

This invention relates to a process for convening $C_5/C_6$ hydrocarbons to aromatic products, e.g., benzene, toluene, etc. The process involves first flowing the $C_5/C_6$ feedstream to a first reaction zone where the $C_5/C_6$ feed is convened to aromatics and $C_3/C_4$ products which are then flowed to a second reaction zone where the $C_3$—$C_4$ compounds are convened to aromatic compound along with formation of hydrogen and fuel gas products. The product stream from the second reaction zone is combined with the products from the first conversion zone and the entire stream separated into the desired components.

6 Claims, 1 Drawing Sheet

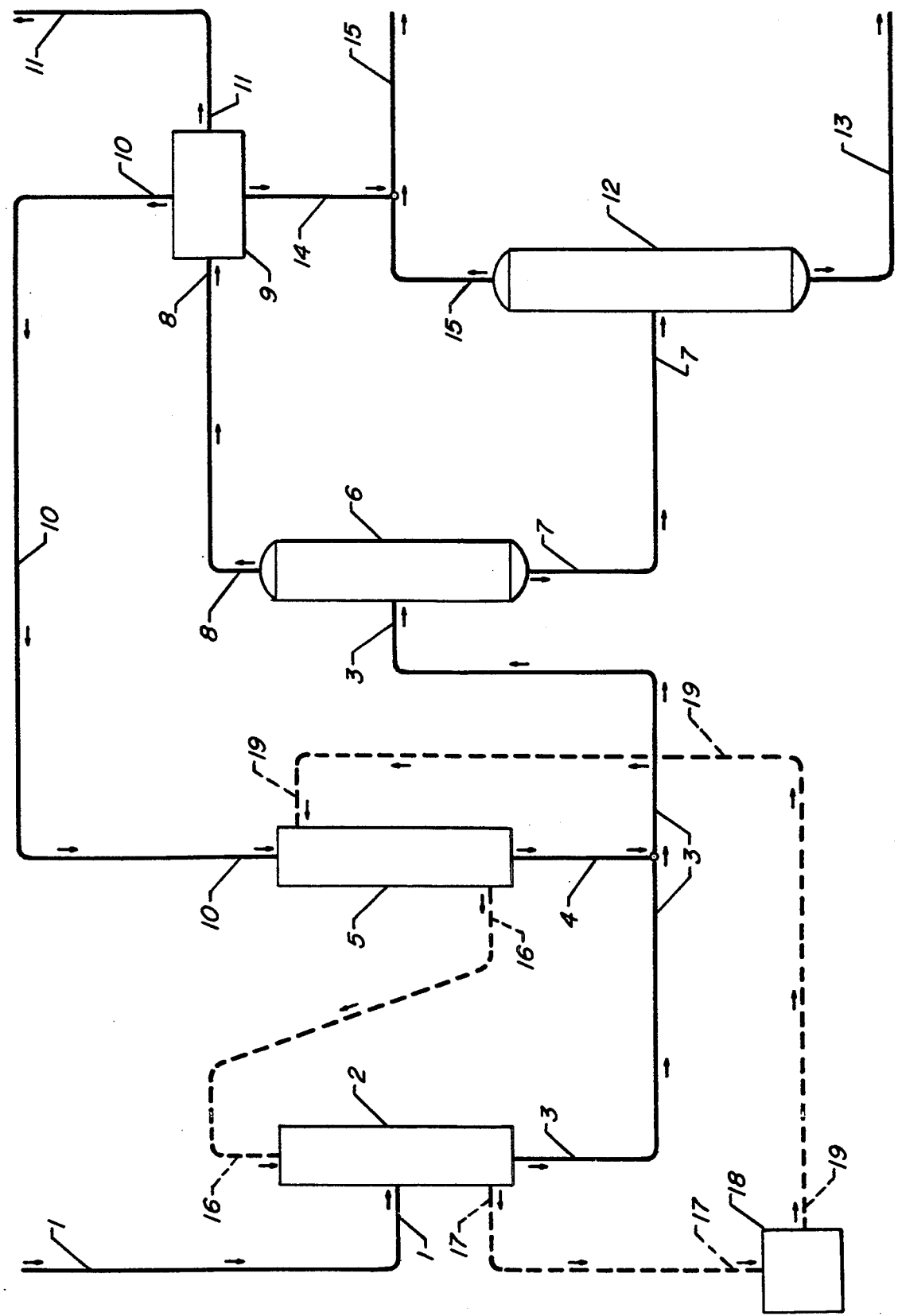

PROCESS FOR PRODUCING AROMATICS FROM A $C_5/C_6$ FEEDSTREAM

FIELD OF THE INVENTION

This invention relates to a process for producing aromatic hydrocarbons from a $C_5/C_6$ feedstream. The process involves converting the $C_5/C_6$ hydrocarbons primarily to $C_3/C_4$ and a small amount of aromatics. Subsequently, the $C_3/C_4$ product is substantially converted to additional aromatic products.

BACKGROUND OF THE INVENTION

Dehydrocyclodimerization (DHCD) is a process in which aliphatic hydrocarbons containing from 2 to 6 carbon atoms per molecule are reacted over a catalyst to produce a high yield of aromatics and hydrogen. This process is well known and is described in detail in U.S. Pat. Nos. 4,654,455 and 4,746,763 which are incorporated by reference. Typically, the dehydrocyclodimerization reaction is carried out at temperatures in excess of 500° C., using dual functional catalysts containing acidic and dehydrogenation components. The acidic function is usually provided by a zeolite which promotes the oligomerization and aromatization reactions, while a non-noble metal component promotes the dehydrogenation function.

Since the product stream from the dehydrocyclodimerization process contains a mixture of compounds, it must undergo several separation steps in order to obtain usable products. A first fractionation zone will separate any unreacted feedstream from a $C_6+$ product stream. The unreacted feedstream is recycled to the dehydrocyclodimerization zone while the product stream is fed to a second fractionation zone to separate the product mixture into benzene, toluene, xylenes and heavier aromatics.

Although the prior art states that $C_2$ to $C_6$ aliphatic hydrocarbons can be used in the dehydrocyclodimerization process, it also cautions that the amount of $C_5$ and $C_6$ hydrocarbons should be kept to a minimum, preferably less than 20 weight percent. The reason for this is that pentanes and hexanes are much more reactive than propane and butane at DHCD operating conditions, thereby forming considerable coke which quickly deactivates the catalyst. Another reason to minimize the amount of pentane in the feedstream is that pentane typically has a high economic value which would not be increased considerably by converting it to aromatics. However, there may be situations where it may be desirable to use a pentane/hexane feedstream to produce aromatic hydrocarbons. For example, $C_5/C_6$ products in remote gas producing regions have a low economic value relative to aromatics. Since the current state of the art would not produce a high yield of aromatics, there is a need to develop a process which would provide a high yield of aromatics from a pentane/hexane feedstream.

Applicants have developed a process which solves this problem. A first step in applicants' process involves contacting the $C_5/C_6$ feedstream with a DHCD catalyst at a temperature of about 300° C. to about 500° C. This operating temperature is about 50° C. to 100° C. lower than is used in a typical DHCD reactor. At this lower temperature the $C_5/C_6$ hydrocarbons are converted to aromatics and $C_3/C_4$ products with the majority of the products being propane and butane. Only small amounts of coke are formed at these lower temperatures. The $C_3/C_4$ hydrocarbons are now contacted with a DHCD catalyst under normal DHCD conditions to produce aromatic products, hydrogen and byproducts. Finally, the aromatic products are separated in the usual manner.

SUMMARY OF THE INVENTION

This invention relates to a process for converting pentane to aromatic hydrocarbons. Accordingly, one embodiment of the invention is a process for the production of aromatic hydrocarbons comprising:

a) flowing a $C_5/C_6$ feedstream into a first reaction zone where said feedstream is contacted with a first solid catalyst at a temperature of about 300° C. to about 500° C., a pressure of about 68 kPa to about 689 kPa, and at a liquid hourly space velocity of about 0.5 to about 10 $hr^{-1}$, thereby converting the feedstream to a first product stream containing aromatic and $C_3$—$C_4$ hydrocarbons;

b) mixing the first product stream from step a) with the second product stream from step d) and flowing it to a separation zone where the mixed product stream is separated into a bottom stream containing $C_5+$ and an overhead product stream containing hydrogen and $C_1$—$C_4$ hydrocarbons;

c) flowing the overhead product stream from step (b) into a cryogenic separation zone in order to separate the overhead product stream into a $C_3$—$C_4$ recycle stream and a hydrogen stream and a $C_1$—$C_2$ fuel gas stream;

d) flowing the $C_3$—$C_4$ recycle stream from step c) to a second reaction zone where the recycle $C_3$—$C_4$ stream is contacted with a second solid catalyst at a temperature of about 40020 C. to about 600° C., a pressure of about 68 kPa to about 689 kPa and a liquid hourly space velocity of about 0.5 to about 10 $hr^{-1}$, thereby producing a second product stream comprising benzene, toluene, xylenes, $C_9+$ aromatics, $C_1$—$C_4$ aliphatic hydrocarbons and hydrogen;

e) flowing the bottom stream from step (b) to a second separation zone operated at conditions effective to separate the bottom stream of step (b) into a $C_6+$ final product stream and a second overhead stream containing fuel gas.

This and other objects and embodiments of this invention will become more apparent after the detailed description of the invention.

BRIEF DESCRIPTION OF THE DRAWING

The Figure is a simplified process flow diagram of one embodiment of the invention showing the formation of aromatic product from a $C_5/C_6$ feedstream as well as separation and recycle of the product and by-products respectively.

DETAILED DESCRIPTION OF THE INVENTION

As stated, this invention relates to a process for the preparation of aromatic hydrocarbons from a $C_5/C_6$ feedstream. The $C_5/C_6$ feedstream is flowed into a first reaction zone where it is contacted with a catalyst in order to convert it to aromatic products and $C_3/C_4$ products. The configuration of the reaction zone and the composition of the catalyst are the same as used for DHCD reaction zones and are thus well known in the art.

Although reaction zones which are used to contact hydrocarbon streams with a catalyst bed are well known in the art, they are briefly described here to provide a background to the subject invention. Usually the reaction zone consists of a moving bed radial flow multistage reactor as described for example in U.S. Pat. Nos. 4,110,081 and 4,403,909 which are incorporated by reference. A moving bed is a catalyst containing system in which the catalyst particles rest upon one another in a dense bed and the inventory of the bed is gradually replaced through the removal of used catalyst at the bottom and the addition of fresh or regenerated catalyst at the top. Further, a radial flow reactor is one in which reactants are flowed radially inward from the periphery of a vertical cylindrical reaction vessel to a cylindrical reactant collection volume which is enclosed by an inner catalyst retention screen which is commonly referred to as the centerpipe of the reactor. Usually the used or deactivated catalyst which is removed from the bottom of the reactor is regenerated and flowed to the top of the reactor. A preferred moving bed reactor system employs a spherical catalyst having a diameter between about 0.4 millimeters and 3.2 millimeters.

The catalyst used in this first reaction zone may be the same or different from that used in the second reaction zone and thus will be referred to as a first solid catalyst. As stated, these catalysts are well known in the art and comprise a zeolitic material, a metallic component and a binder. U.S. Pat. Nos. 4,654,455, 4,746,763 and 5,169,812, which are incorporated by reference, describe DHCD catalyst and methods of preparing them. A brief description of these catalysts will be presented for completeness.

The zeolites which may be used are any of those which have a Si:Al ratio greater than about 10 and preferably greater than 20 and a pore diameter of about 5 to 6 Angstroms. Specific examples of zeolites which can be used are the ZSM family of zeolites. Included among this ZSM family are ZSM-5, ZSM-8, ZSM-11, ZSM-12 and ZSM-35. The preparation of these ZSM-type zeolites is well known in the art and generally are prepared by crystallizing a mixture containing an alumina source, a silica source, an alkali metal source, water and a tetraalkyl ammonium compound or its precursor. The amount of zeolite present in the catalyst can vary considerably but usually is present in an amount from about 30 to about 90 weight percent and preferably from about 50 to about 70 weight percent of the catalyst.

A second component of these catalysts is a phosphorus containing alumina (hereinafter referred to as aluminum phosphate) component. The phosphorus may be incorporated with the alumina in any acceptable manner known in the art. One preferred method of preparing this aluminum phosphate is that described in U.S. Pat. No. 4,629,717 which is incorporated by reference. The technique described in the '717 patent involves the gellation of a hydrosol of alumina which contains a phosphorus compound using the well-known oil drop method. Generally this technique involves preparing a hydrosol by digesting aluminum in aqueous hydrochloric acid at reflux temperatures of about 80° to 105° C. The ratio of aluminum to chloride in the sol ranges from about 0.7:1 to about 1.5:1 weight ratio. A phosphorus compound is now added to the sol. Preferred phosphorus compounds are phosphoric acid, phosphorous acid and ammonium phosphate. The relative amount of phosphorus and aluminum expressed in molar ratios ranges from about 1:1 to 1:100 on an elemental basis.

The resulting aluminum phosphate hydrosol mixture is now gelled. One method of gelling this mixture involves combining a gelling agent with the mixture and then dispersing the resultant combined mixture into an oil bath or tower which has been heated to elevated temperatures such that gellation occurs with the formation of spheroidal particles. The gelling agents which may be used in this process are hexamethylene tetraamine, urea or mixtures thereof. The gelling agents release ammonia at the elevated temperatures which sets or converts the hydrosol spheres into hydrogel spheres. The spheres are then continuously withdrawn from the oil bath and typically subjected to specific aging and drying treatments in oil and in ammoniacal solution to further improve their physical characteristics. The resulting aged and gelled particles are then washed and dried at a relatively low temperature of about 93° C. to about 149° C. (200°–300° F.) and subjected to a calcination procedure at a temperature of about 450° C. to about 703° C. (850°–1300° F.) for a period of about 1 to about 20 hours. The amount of phosphorus containing alumina component present (as the oxide) in the catalyst can range from about 10 to about 70 weight percent and preferably from about 30 to about 50 weight percent.

The zeolite and aluminum phosphate binder are mixed and formed into particles by means well known in the art such as gellation, pilling, nodulizing, marumerizing, spray drying, extrusion or any combination of these techniques. A preferred method of preparing the zeolite/aluminum phosphate support involves adding the zeolite either to an alumina sol or a phosphorus compound, forming a mixture of the alumina sol/zeolite/phosphorus compound which is now formed into particles by employing the oil drop method described above. The particles are calcined as described above to give a support.

Another component of these catalysts is a gallium component. The gallium component may be deposited onto the support in any suitable manner known to the art which results in a uniform dispersion of the gallium. Usually the gallium is deposited onto the support by impregnating the support with a salt of the gallium metal. The particles are impregnated with a gallium salt selected from the group consisting of gallium nitrate, gallium chloride, gallium bromide, gallium hydroxide, gallium acetate, etc. The amount of gallium which is deposited onto the support varies from about 0.1 to about 5 weight percent of the finished catalyst expressed as the metal.

The gallium compound may be impregnated onto the support particles by any technique well known in the art such as dipping the catalyst into a solution of the metal compounds or spraying the solution onto the support. One preferred method of preparation involves the use of a steam jacketed rotary dryer. The support particles are immersed in the impregnating solution contained in the dryer and the support particles are tumbled therein by the rotating motion of the dryer. Evaporation of the solution in contact with the tumbling support is expedited by applying steam to the dryer jacket. After the particles are completely dry, they are heated under a hydrogen atmosphere at a temperature of about 500° to about 700° C. for a time of about 1 to about 15 hours. Although a pure hydrogen atmosphere is preferred to reduce and disperse the gallium, the hydrogen may be diluted with nitrogen. Alternatively, it is envisioned that the reduction and dispersion can be done in situ in the actual reactor vessel used for dehydrocyclodimerization by using either pure hydrogen or a mixture of hydrogen and hydrocarbons. Next the hydrogen treated particles are heated in air and steam at a temperature of about 400° to about 700° C. for a time of about 1 to about 10 hours. The amount of steam present in the air varies from about 1 to about 40 percent.

A particularly preferred catalyst is one described in U.S. Pat. No. 5,169,812. This reference describes a gallium/aluminum phosphate/zeolite catalyst which has been treated with an aqueous solution of a weakly acidic ammonium salt or a dilute acid solution, e.g., ammonium chloride or hydrochloric acid.

As stated, the $C_5/C_6$ feedstream is converted to aromatics and $C_3/C_4$ products. The relative amount of these two products, as well as formation of coke by-product, is determined by whether a fresh or a partially deactivated DHCD catalyst is used. By partially deactivated is meant a catalyst that has lost about 50% of its initial activity. A fresh catalyst will produce more $C_3/C_4$ (versus aromatics) than a partially deactivated catalyst while also increasing coke formation. Accordingly, in order to maximize the formation of aromatics, it is preferred to use a partially deactivated DHCD catalyst. Such a catalyst should give about a 20–30% conversion to aromatics.

The reaction zone is operated at a temperature of about 300° C. to about 500° C., preferably about 400° C. to about 500° C., a pressure of about 68 kPa to about 689 kPa and a liquid hourly space velocity from about 0.5 to about 10 hr$^{-1}$. As will be shown the temperature at which this reaction zone is operated is considerably lower than a conventional DHCD zone. The product from this reaction zone will contain propane, butane, $C_6^+$ aromatics[1], methane, ethane and hydrogen. This product stream is separated into an aromatics stream and a $C_3/C_4$ stream.

[1] As used throughout this specification the term $C_X^+$ refers to hydrocarbons having x number of carbon atoms or greater, whereas the term $C_X^-$ refers to hydrocarbons having x number of carbon atoms or less. Thus, $C_6^+$ means six (6) carbon atoms or greater, whereas $C_5^-$ means five (5) carbon atoms or less.

The $C_3/C_4$ stream is flowed to a second reaction zone which is a conventional DHCD zone using a second solid catalyst and is operated at a temperature of about 400° C. to about 600° C., preferably about 500° C. to about 600° C., a pressure of about 68 kPa to about 689 kPa and a liquid hourly space velocity of about 0.5 to about 10 hr$^{-1}$. The effluent from this second reaction zone will contain hydrogen, $C_1/C_2$, unreacted $C_3/C_4$ hydrocarbons, benzene, toluene, xylenes and $C_9^+$ aromatics. This product stream is combined with the product stream from the first reaction zone and processed in order to separate the various components.

The Figure illustrates one embodiment of the invention. Those skilled in the art will recognize that this process flow diagram has been simplified by the elimination of many pieces of process equipment including heat exchangers, process control systems, pumps, fractionation column overhead and reboiler systems, etc. which are not necessary to an understanding of the process. It may also be readily discerned that the process flow presented in the drawings may be modified in many aspects without departing from the basic overall concept of the invention. Referring now to the Figure, a feedstream of $C_5/C_6$ hydrocarbons is flowed into reaction zone 2 via line 1. As stated, within the reaction zone, the $C_5/C_6$ stream is contacted with a first solid catalyst under mild conversion conditions effective to convert the $C_5/C_6$ stream primarily to $C_3/C_4$ hydrocarbons and aromatics (about 30%) plus a small amount of coke. The product is removed via line 3 and is combined with line 4 which contains the product stream from the second reaction zone 5 and flowed into separation zone 6.

Into the second reaction zone 5 is flowed a recycle stream via line 10 from cryogenic separation zone 9. This recycle stream contains $C_3/C_4$ hydrocarbons. Within the second reaction zone the recycle stream is contacted with a second solid catalyst under DHCD conditions effective to convert a significant portion of the $C_3/C_4$ stream to aromatic hydrocarbons.

The combined product streams from first reaction zone 2 and second reaction zone 5 are combined by flowing line 4 from the second reaction zone 5 into line 3 from reaction zone 2. This combined product stream is flowed via line 3 to first separation zone 6 which is operated at conditions effective to provide a first separation zone bottoms stream and a first separation zone overhead stream. The first separation zone bottoms stream is removed via line 7 and contains aromatics plus small quantities of dissolved hydrogen and up to $C_5$ hydrocarbons, i.e., $C_5^-$ hydrocarbons, while the first separation zone overhead stream which contains $C_4^-$ and hydrogen is removed via line 8.

The $C_4^-$ and hydrogen contained in the first separation zone overhead stream is flowed via line 8 into cryogenic separation zone 9. In cryogenic separation zone 9, conditions are controlled to separate, hydrogen and light gases ($C_1$ and $C_2$) from the $C_3$ and $C_4$ components. The hydrogen is exported via line 11, while the light gases are removed via line 14. The $C_3$ and $C_4$ components are removed via line 10 and flowed into DHCD zone 5.

The aromatics and other components contained in the first separation zone bottoms stream is flowed via line 7 into a second separation zone 12. This second separation zone is operated at conditions effective to provide a second separation zone bottoms stream which contains aromatics ($C_6^+$) and a second separation zone overhead stream which contains hydrogen and fuel gas products. The second bottoms stream is removed via line 13 and can be further processed to obtain separate streams of benzene, toluene and xylenes. The second separation zone overhead stream is removed via line 15 combined with line 14 and vented.

The second separation zone can be either a conventional distillation/fractionation zone or it can be an extractive distillation zone. Both types of separation zones are well known in the art. For example, in an extractive distillation zone the feedstream is contacted with an aromatic selective solvent stream at distillation conditions to separate aromatics from non-aromatic components. Further details may be found in U.S. Pat. No. 5,225,072 which is incorporated by reference.

An optional part of the embodiment presented in the Figure involves a continuous catalyst regeneration scheme. In this scheme (shown in dashed lines) deactivated catalyst (second solid catalyst) from the bottom of reactor 5 is flowed via line 16 to the top of reactor 2. As the catalyst further deactivates by progressing down reactor 2, it is removed from the bottom of reactor 2 via line 17 and flowed to regeneration zone 18 where the spent catalyst is regenerated and then flowed to the top of reactor 5 via line 19.

Regeneration of the catalyst is carried out in regeneration zone 18 by means well known in the art. One particular regeneration method is disclosed in U.S. Pat. No. 4,859,643 which is incorporated by reference. Usually the catalyst which can have up to 20 weight percent coke is passed through a combustion zone where it is mixed with air at temperatures of 900° F. to about 1000° F. Next the catalyst is dried in a drying zone to remove water formed in the combustion zone. Further details may be found in the '643 patent and references therein.

We claim as our invention:

1. A process for the production of aromatic hydrocarbons comprising:
   a) flowing a $C_5/C_6$ feedstream into a first reaction zone where said feedstream is contacted with a first solid catalyst at a temperature of about 300° C. to about 500° C., a pressure of about 68 kPa to about 689 kPa, and at a liquid hourly space velocity of about 0.5 to about 10 $hr^{-1}$, thereby converting the feedstream to a first product stream containing aromatics and $C_3$—$C_4$ hydrocarbons;
   b) mixing the first product stream from step a) with a second product stream from step d) to give a mixed product stream and flowing it to a separation zone where the mixed product stream is separated into a bottom stream containing $C_5^+$ hydrocarbons and an overhead product stream containing hydrogen and $C_1$—$C_4$ hydrocarbons;
   c) flowing the overhead stream from step (b) into a cryogenic separation zone in order to separate the overhead product stream into a $C_3$—$C_4$ recycle stream and a hydrogen stream and a $C_1$—$C_2$ fuel gas stream;
   d) flowing the $C_3$—$C_4$ recycle stream from step (c) to a second reaction zone where the recycle $C_3$—$C_4$ stream is contacted with a second solid catalyst at a temperature of about 400° C. to about 600° C., a pressure of about 68 kPa to about 689 kPa and a liquid hourly space velocity of about 0.5 to about 10 $hr^{-1}$, thereby producing a second product stream comprising benzene, toluene, xylenes, $C_9^+$ aromatics, $C_1$—$C_4$ aliphatic hydrocarbons and hydrogen;
   e) flowing the bottom stream from step (b) to a second separation zone operated at conditions effective to separate the bottom stream of step (b) into a $C_6^+$ final product stream and a second overhead stream containing fuel gas.

2. The process of claim 1 where the first reaction zone is operated at a temperature of about 400° C. to about 500° C.

3. The process of claim 1 where the second reaction zone is operated at a temperature of about 500° C. to about 600° C.

4. The process of claim 1 further characterized by the steps of:
   (i) removing deactivated solid catalyst from the bottom of the second reaction zone and flowing it to the top of the first reaction zone;
   (ii) removing catalyst from the bottom of the first reaction zone and flowing it to a regeneration zone; and
   (iii) regenerating said catalyst in the regeneration zone and flowing the regenerated catalyst into the top of the second reaction zone.

5. The process of claim 1 where the first and second solid catalysts are the same and comprise a zeolite component, a gallium component and an aluminum phosphate binder.

6. The process of claim 1 where the second separation zone is an extractive distillation zone.

* * * * *